United States Patent

Koscher et al.

[11] Patent Number: 5,690,673
[45] Date of Patent: Nov. 25, 1997

[54] SURGICAL INSTRUMENT

[76] Inventors: Stephan Koscher, Lachstrasse 53; Johann Wurtz, Semmelweiss-Strasse 32, both of D-78549 Spaichingen, Germany

[21] Appl. No.: 604,825
[22] Filed: Feb. 23, 1996

[30] Foreign Application Priority Data

Mar. 9, 1995 [DE] Germany .................. 195 08 186.2

[51] Int. Cl.⁶ .................................................. A61B 17/00
[52] U.S. Cl. .................... 606/205; 606/174; 128/751
[58] Field of Search ................. 606/1, 170, 174, 606/205–210, 51, 52; 128/750–755; 81/419

[56] References Cited

U.S. PATENT DOCUMENTS 5,234,460  8/1993  Stouder, Jr. .................. 606/205
5,251,638  10/1993  Cottone, Jr. et al. .......... 606/206
5,308,357  5/1994  Lichtman ...................... 606/206

Primary Examiner—William Lewis
Attorney, Agent, or Firm—Bachman & LaPointe, P.C.

[57] ABSTRACT

In a surgical instrument having at least one jaw part which is attached to at least one handle part by a pulling or pushing element which is movable along its lengthwise axis (A), there is associated with the pulling or pushing element a pin or the like which engages into a recess which is associated with the handle part and the axis (B) of which extends at an angle (w) to the lengthwise axis (A) of the pulling or pushing element.

14 Claims, 2 Drawing Sheets

5,690,673

SURGICAL INSTRUMENT

BACKGROUND OF THE INVENTION

The present invention relates to a surgical instrument having at least one jaw part which is attached to at least one handle part via a pulling or pushing element which is movable along its lengthwise axis.

Such surgical instruments are available on the market and are used in many forms and embodiments. They serve to carry out surgical procedures, for instance, in the human body. This includes, among other things, cutting, clamping, removing tissue samples, etc.

In this action, as a rule, two jaw parts cooperate with each other, in which connection one jaw part may also be stationary and the other movable, or else both jaw parts may be movable.

The moving of the jaw part or parts is effected in most cases by the actuating of handle parts which are rotatably connected with each other around a pivot pin. The corresponding pulling or pushing element is, however, only attached to one handle part, which is then movable relative to the other handle part.

As a rule, the attachment the of pulling or pushing element to the handle part is effected in the manner that the handle part is arranged at an angle to the pulling or pushing element. The surgical instrument is then held in the manner of a pistol.

Admittedly, such surgical instruments require a large expenditure of force on the part of the surgeon in a lengthy operation and their exact guidance is difficult. The sense of feel for the handling of this surgical instrument declines with the length of the operation.

Furthermore, upon the opening and closing of the jaw parts, the jaw parts are generally moved with respect to the place in the human body which is to be worked on, so that precise access suffers.

Other problems concern the assurance of the surgical instrument against the danger of breakage since pins and joints are made very fine. As part of modern hygienic requirements, it is furthermore indispensable that the instrument be capable of being easily cleaned.

SUMMARY OF THE INVENTION

The object of the present invention is substantially to improve the previously known surgical instruments of the above-indicated type, substantially facilitate the handling of them, make them safer, and satisfy the increasing hygienic demands.

In order to achieve this object, a pin or the like is associated with the pulling or pushing element, the pin engaging in a recess associated with the handle part the axis of which extends at an angle to the lengthwise axis of the pulling or pushing element.

By this arrangement, assurance is had that upon the opening or closing of the handle part, the pin and thus the pulling or pushing element is guided precisely along the lengthwise axis of the pulling or pushing element. The instrument itself, however, is not moved, so that its position and particularly the position of the jaw with respect to a tissue which is to be handled can remain absolutely fixed in the same place. By the direct transfer of the pulling or pushing function from the handle part to the jaw part, the surgeon is provided with a considerable better feel for the handling of the surgical instrument.

The novel design of the connection without outside joints assures a shake-free opening and closing motion. This refers, in particular, to the preferred embodiment in which both handle parts are developed and movable absolutely symmetrically. This will be described further below.

The previous disadvantages of outside joint constructions, such as for instance the disturbance in connection with different handle positions, the danger of clamping and damaging protective gloves, the dirtying of inaccessible parts which are difficult to clean, etc., are eliminated. Furthermore, small pins and joints can be dispensed with, so that the danger of breakage is substantially reduced.

Mention should also be made of an optimal transfer of force from the handle part to the distal end, which permits a substantially greater closing pressure than in the case of traditional instruments. This is particularly true of instruments which are so closed upon clamping that the front region of a clamping jaw is first closed and then the rear region. This is a substantial advantage, particularly in the case in intestinal forceps.

It should furthermore be mentioned that the surgeon no longer holds the surgical instrument in the manner of a revolver, but can engage his hand from above into the two handle holes, and that the opening and closing of the handle parts takes place in an approximately horizontal plane. In this way, handling is substantially facilitated and the expenditure of force reduced.

In a preferred embodiment, the aforementioned recess in which the pin slides is developed as a slot which extends at an angle to the lengthwise axis of the pulling or pushing element. Upon the turning of the handle part, this slot continuously intersects the lengthwise axis, but in each case in a different position along this lengthwise axis.

The slot is preferably developed in a tongue which extends from a disk element of the handle part. The handle part itself is turnable around this disk element, an approximately central opening being provided in the disk element, this opening being replaced, in the position of use, by the above-mentioned pivot pin. The slot extends approximately tangentially to said opening.

The disk element adjoins, preferably as one piece, a coupling piece which, in its turn passes into a handle bar, the latter, in its turn, passing into a handle opening. Disk element, handle bar and handle opening lie in the same plane. The pull wire also lies in this plane, the lengthwise axis of the pull wire, when the handle part is closed, extending approximately paraxially to the handle bar.

The handle part is preferably arranged in a housing shell and fastened there via the pivot pin. This housing shell surrounds the entire movement mechanism so that, as mentioned above, joint structures on the outside are avoided. This housing shell preferably has corresponding openings for the introducing of a disinfectant. Here, many possibilities, all covered by the invention, are conceivable.

Another essential feature of the invention relates to the precise guiding of the pulling or pushing element by means of the above-mentioned pin. In order that the pin cannot move away laterally, it is guided in a guide groove in the housing shell or in a cover attaching the housing shell. This guide groove also extends in the direction of the lengthwise axis of the pulling or pushing element.

A better assembling of the instrument is assured in the manner that the pulling or pushing element is also detachably connected to the pin. This is done by a ball socket which is developed in the pin and which serves to receive a ball which, in its turn, is formed on the pulling or pushing element.

In the preferred embodiment of the invention, the two handle parts are movable symmetrically to each other. In corresponding manner, they are also developed symmetrically and have the slots arranged as mirror images to the lengthwise axis of the pulling or pushing element. These slots are then each passed through by a pin, which pins are guided in a guide groove in the housing shell or cover.

The two pins are preferably connected by a plate which is arranged between the two disk elements or tongues which have the slots. This plate has a diameter which is larger than that of the pin, as a result of which a tilting of this pull-wire bushing upon actuation is avoided.

BRIEF DESCRIPTION OF THE DRAWINGS

Further advantages, features and details of the invention will be evident from the following description of preferred embodiments and from the drawings, in which.

DETAILED DESCRIPTION OF PREFERRED EMBODIMENTS

Figure 1:
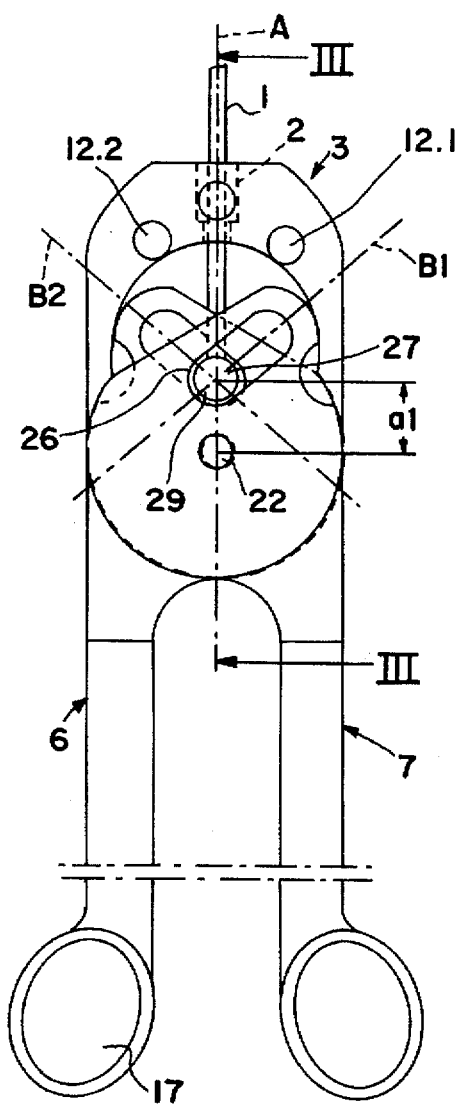
FIG. 1 is a top view of an opened part of a surgical instrument.
Figure 3:
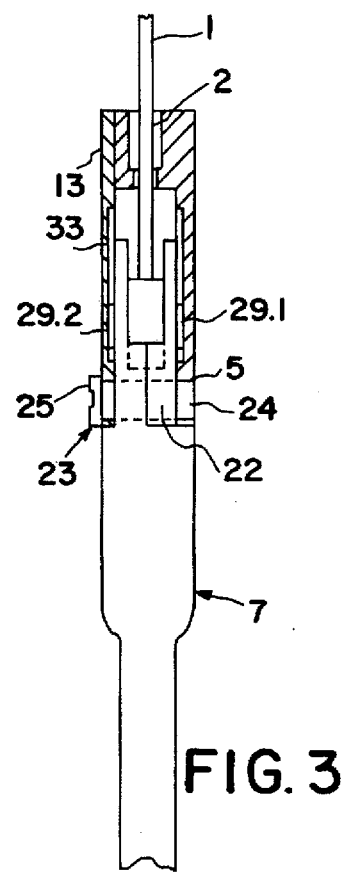
FIG. 3 is a cross section through the surgical instrument with cover in accordance with FIG. 1, seen along the line III—III.
Figure 2:
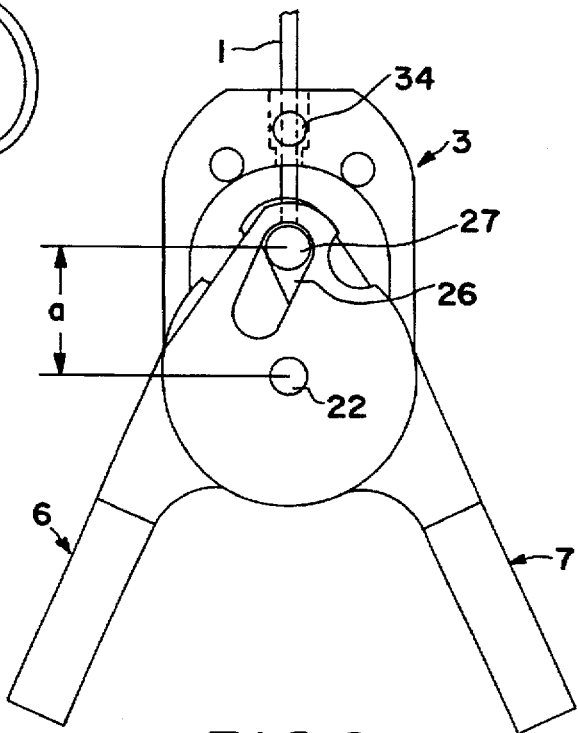
FIG. 2 is a top view of a part of the surgical instrument of FIG. 1, shown in a further position of use.

FIGS. 1 to 3 show essentially only those elements of a surgical instrument in accordance with the invention which serve for the actuating of a pull wire 1. This pull wire 1 extends customarily to a tweezer, cutting, clamping or similar jaw (not shown), corresponding jaw parts being moved by the pull wire 1. Ordinarily, the pull wire 1 is surrounded by an outer tube, also not shown in detail, which is inserted into a stepped hole 2. This stepped hole 2 is formed on the front side of housing shell 3.

Figure 4:
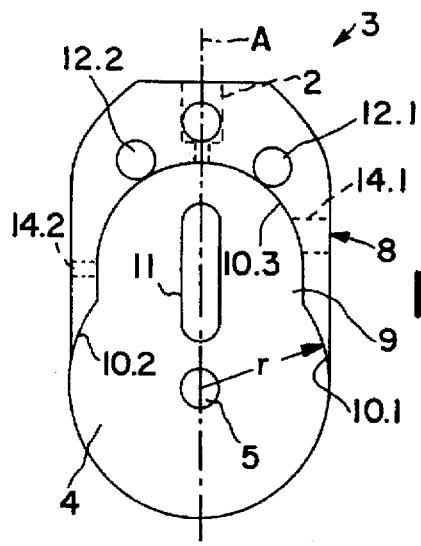
FIG. 4 is a top view of a housing shell of the surgical instrument of FIG. 1.

This housing shell 3 is shown by itself in FIG. 4. It has a bottom 4 in which a threaded hole 5 is formed. This threaded hole 5 forms a center point for a hinge joint to be described further below, for handle parts 6 and 7.

Above the threaded hole 5, a rim 8 which partially surrounds a trough 9 commences. On both sides, the rim 8 passes with a curved inner wall 10.1 and 10.2 having a radius r. Adjoining each of the inner walls 10.2 and 10.1 there is an approximately semicircularly curved inner wall 10.3.

Within the trough 9, a slot-like guide groove 11 is developed towards the threaded hole 5 and in the direction of a lengthwise axis A of the pull wire 11.

The rim 8 is provided with two further mounting holes 12.1 and 12.2 which serve to receive screws (not shown in detail) for a cover 13 indicated in FIG. 3. This cover 13 closes off the trough 9 and has a contour corresponding to the top view of the housing shell 3 shown in FIG. 4. On the side, two flush openings 14.1 and 14.2 are furthermore developed in the rim 8.

Figure 5:
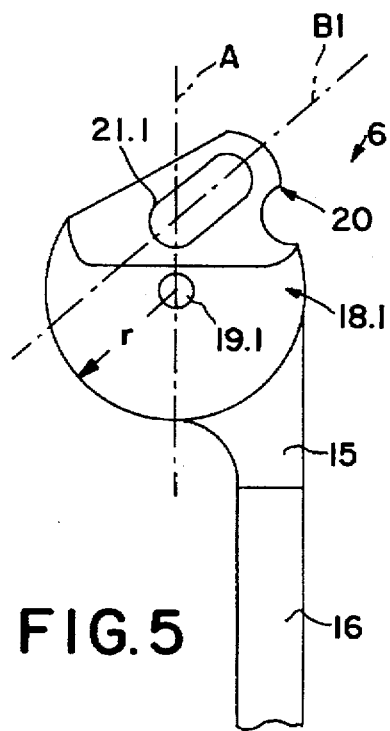
FIGS. 5 and 6 are top views of two handle parts of the surgical instrument of FIG. 1.
Figure 6:
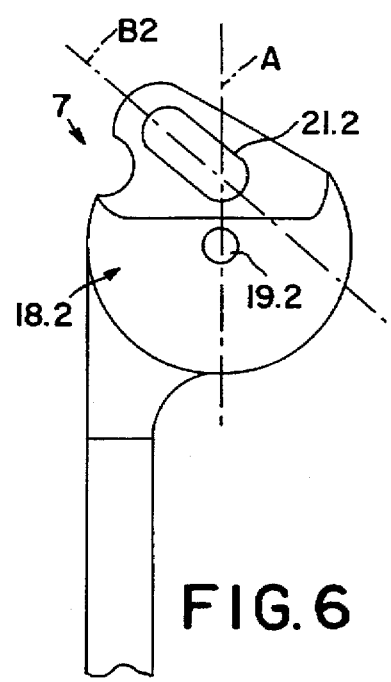

As shown in FIGS. 5 and 6, the handle parts 6 and 7 are developed as mirror images of each other. On the one side, a coupling piece 15 is adjoined by a handle bar 16 which, as indicated in FIG. 1, passes into a handle hole 17. The finger of a surgeon can engage into the handle hole 17.

On the other side there is developed on the coupling piece 15 a disk element 18.1 and 18.2 which is developed in part as somewhat more than a semicircle with a radius R. This disk element has an opening 19.1 and 19.2 in its center.

Above the opening 19.1 and 19.2 a tongue 20 in which a slot 21.1 and 21.2 is formed adjoins the disk element 18.1 and 18.2. The slot 21.1 of the one handle part 6 has an axis $B_1$ which extends at an angle w inclined to the lengthwise axis A when the handle parts 6 and 7 are in a position of use shown in FIG. 1.

The second handle part 7 also has a slot 21.2, which also has a lengthwise axis $B_2$. This lengthwise axis $B_2$ is also inclined to the lengthwise axis A, but is a mirror image to the lengthwise axis $B_1$, as con be noted in FIG. 1.

In the different positions of use shown in FIGS. 1 and 2, the two disk elements 18.1 and 18.2 of the two handle parts 6 and 7 lie one above the other, the two openings 19.1 and 19.2 being congruent to each other. Through these openings 19.1 and 19.2 there is inserted a pivot shank 22 of a screw 23, a thread 24 adjoining the shank 22 on one side and a screw head 25 adjoining it on the other side. The threaded piece 24 is inserted into the threaded hole 5 while the screw head 25 holds the cover 13, together with screws, not shown in detail, which engage into the mounting holes 12.1 and 12.2.

Figure 7:
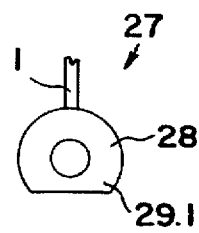
FIG. 7 is a top view of a pull-wire bushing for the handle parts.
Figure 8:
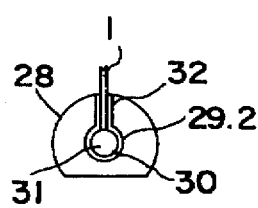
FIG. 8 is a top view of the pull-wire bushing of FIG. 7, shown in position of use.
Figure 9:
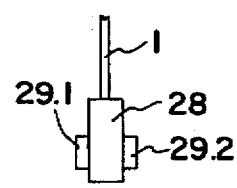
FIG. 9 is a side view of the pull-wire bushing of FIG. 8.

In this position of use, the two slots 21.1 and 21.2 overlap each other upon the turning of the handle parts 6 and 7 around the pivot shaft 22 in every position of rotation shown, so that a congruent recess 26 is formed the contour of which, while it changes slightly, is always, however, sufficiently large to receive a pull-wire bushing 27. This pull-wire bushing is shown in further detail in FIGS. 7 through 9. It has a central plate 28 which is curved in more than a semicircle, adjoined on both sides by pins 29.1 and 29.2.

A ball socket 30 to receive a ball 31 which is connected to the pull wire 1 is formed in the pin 29.2. From the ball socket 30 a groove 32 also extends in the plate 28 so that the pull wire 1 and the ball 31 can be connected detachably to the pull-wire bushing 27.

The pins 29.1 and 29.2 are guided in the corresponding guide grooves 11 in the housing shell 3 and in a guide groove 13, shown in FIG. 3, in the cover 13 after passage through the slots 21.1 and 21.1, so that the pull-wire bushing 27 can be displaced only along the lengthwise axis A.

The plate 28, which has a larger diameter than the pin 29, lies between the two disk elements 18.1 and 18.2 of the handle parts 6 and 7 and prevents a tilting of the pull-wire bushing 27.

Upon the turning of the handle parts 6 and 7 around the pivot shank 22 the common recess 26 of the two slots 21.1 and 21.2 travels along the lengthwise axis A. In this connection, the pull-wire bushing 27 is also carried along this lengthwise axis A whereby a corresponding jaw part is actuated.

It is obvious that the slots 21.1 and 21.2 and the handle parts 6 and 7 also could be arranged the other way around, so that upon the opening and closing of the handle parts 6 and 7, a pushing action is produced on the pull wire 1 rather than a pulling action.

The assembly of this surgical instrument of the invention is effected as follows with respect to the region of the actuating mechanism:

The handle part 6 is inserted in the housing shell 3. Thereupon, the pull wire 1 is inserted with the ball 31 in the ball socket 30 of the pull-wire bushing 27. The pull wire is then pushed through the stepped hole 2 and the pin 29.1 is inserted into the slot 21.2 and the guide groove 11. The handle part 6 is then placed on, the pin 29.2 engaging through the slot 21.1.

The cover 13 can now be placed on and be fastened by screws in the mounting holes 12.1 and 12.2, as well as by the screw 23. In this connection, the pivot shank 22 of the screw 23 passes through the opening 19.1 and 19.2 of the handle parts 6 and 7 and with the threaded piece 24 engages into the threaded hole in the housing shell 3.

For the opening of the jaw part, the handle parts 6 and 7 are in the open position of use shown in FIG. 2, the pull-wire bushing 27 having its greatest distance a from the pivot shank 22. If now, for instance, a cutting or clamping process is to be carried out with corresponding jaw parts, then the handle parts 6 and 7 are closed until they are in the position of use shown in FIG. 1. In this connection, a distance $a_1$ of the pull-wire bushing 27 from the turn shank 22 is minimized, so that a pulling action has been exerted on the pull wire.

In the housing shell 3, within the region of the stepped hole 2, there is furthermore developed a transverse hole 34. This transverse hole 34 serves to receive a lock screw (not shown in detail) by which the pull wire 1 can be clamped fast. In this way, unintentional actuation of jaw parts is avoided.

We claim:

1. A surgical instrument which comprises: at least one jaw part; at least one handle part connected with said jaw part; a recess connected to said handle part, wherein said recess has an axis thereof; a pulling or pushing element connecting said jaw and handle parts and having a lengthwise axis and being movable along said lengthwise axis; pin means engaging into said recess, wherein the axis of the recess extends at an angle to the lengthwise axis of the pulling or pushing element; and a disk element extending from said handle part and having a tongue thereof, wherein said recess is formed in said tongue.

2. A surgical instrument according to claim 1, wherein said handle part turns around a pivot shank which extends in the lengthwise axis.

3. A surgical instrument according to claim 1, wherein the recess is developed as a slot which extends inclined at an angle to the lengthwise axis.

4. A surgical instrument according to claim 2, including an opening to receive the pivot shank provided approximately centrally in the disk element.

5. A surgical instrument according to claim 4, wherein the disk element is provided on a coupling piece connected to said handle part, and wherein adjoining said coupling piece is a handle bar having a handle hole therein.

6. A surgical instrument which comprises: at least one jaw part; at least one handle part connected with said jaw part; a recess connected to said handle part, wherein said recess has an axis thereof; a pulling or pushing element connecting said jaw and said handle parts and having a lengthwise axis and being movable along said lengthwise axis; pin means engaging into said recess, wherein the axis of the recess extends at an angle to the lengthwise axis of the pulling or pushing element; and wherein the handle part turns around a pivot shank and is held in a housing shell, and wherein said housing shell is covered by a cover, at least one of the housing shell and cover including a guide groove for guiding the pin means.

7. A surgical instrument according to claim 6, wherein the guide groove extends in the direction of the lengthwise axis.

8. A surgical instrument according to claim 7, wherein the housing shell has a bottom and a rim which forms a trough for receiving the pin means.

9. A surgical instrument according to claim 8, wherein the rim includes a stepped hole through which the pulling or pushing element is inserted.

10. A surgical instrument according to claim 9, including a tube surrounding the pulling or pushing element, wherein said tube is inserted through the stepped hole.

11. A surgical instrument which comprises: at least one jaw part; at least one handle part connected with said jaw part; a recess connected to said handle part, wherein said recess has an axis thereof; a pulling or pushing element connecting said jaw and handle parts and having a lengthwise axis and being movable along said lengthwise axis; pin means engaging into said recess, wherein the axis of the recess extends at an angle to the lengthwise axis of the pushing or pulling element; and wherein the pin means has a ball socket to receive a ball which is coupled with the pulling or pushing element.

12. A surgical instrument according to claim 11, including a plate having a larger diameter than the pin means and connected with the pin means.

13. A surgical instrument which comprises: at least one jaw part; at least one handle part connected with said jaw part; a recess connected to said handle part, wherein said recess has an axis thereof, a pulling or pushing element connecting said jaw and handle parts and having a lengthwise axis and being movable along said lengthwise axis; pin means engaging into said recess, wherein the axis of the recess extends at an angle to the lengthwise axis of the pushing or pulling element; including two handle parts connected to each other via a pivot shank, wherein each handle part includes a handle part recess, which recesses are arranged as mirror images of each other around the lengthwise axis of the pushing or pulling element, wherein the axis of each recess extends inclined at an angle to the lengthwise axis; and wherein said pin means are pins which engage through the recesses and into a plate having guide grooves extending on both sides of said plate.

14. A surgical instrument according to claim 12, including disk elements extending from each handle part, wherein the plate is arranged between the two disk elements.

* * * * *